United States Patent
Xu et al.

(10) Patent No.: US 9,593,059 B2
(45) Date of Patent: Mar. 14, 2017

(54) PROCESS FOR THE HYDRATION OF MIXED BUTENES TO PRODUCE MIXED ALCOHOLS

(75) Inventors: Wei Xu, Dhahran (SA); Farhan M. Al-Shahrani, Dhahran (SA); Abdennour Bourane, Ras Tanura (SA); Stephan Ralf Vogel, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 33 days.

(21) Appl. No.: 13/977,860

(22) PCT Filed: Jan. 9, 2012

(86) PCT No.: PCT/IB2012/000145
§ 371 (c)(1),
(2), (4) Date: Oct. 16, 2013

(87) PCT Pub. No.: WO2012/095744
PCT Pub. Date: Jul. 19, 2012

(65) Prior Publication Data
US 2014/0039226 A1    Feb. 6, 2014

Related U.S. Application Data

(60) Provisional application No. 61/431,158, filed on Jan. 10, 2011.

(51) Int. Cl.
C07C 29/04    (2006.01)
C10L 1/182    (2006.01)
(Continued)

(52) U.S. Cl.
CPC ............. *C07C 29/04* (2013.01); *C07C 31/10* (2013.01); *C10G 50/00* (2013.01); *C10L 1/143* (2013.01);
(Continued)

(58) Field of Classification Search
CPC combination set(s) only.
See application file for complete search history.

(56) References Cited

U.S. PATENT DOCUMENTS 2,130,669 A      9/1938   Lewis
3,950,442 A  *   4/1976   Vogel et al. .................. 568/899
(Continued)

FOREIGN PATENT DOCUMENTS

WO      2011/001285 A1      1/2011

OTHER PUBLICATIONS

"Butenes" in Ullmann's Encyclopedia of Industrial Chemistry, Obenaus et al., Published Online: Jun. 15, 2000, DOI: 10.1002/14356007.a04_483, Copyright © 2002 by Wiley-VCH Verlag GmbH & Co. KgaA, pp. 1-14.*

(Continued)

*Primary Examiner* — Karl J Puttlitz
(74) *Attorney, Agent, or Firm* — Abelman, Frayne & Schwab

(57) ABSTRACT

Mixed butenes from a cracking process, or raffinates of MTBE or tert-butyl alcohol (TBA), are simultaneously hydrated using water in the presence of a catalyst to produce sec-butyl alcohol (SBA) and tert-butyl alcohol as the principal products, the mixed butanols having utility as fuel additives, e.g., as oxygenates and octane enhancers to replace MTBE, and as a neat fuel.

7 Claims, 1 Drawing Sheet

(51) Int. Cl.
*C07C 31/10* (2006.01)
*C10L 1/14* (2006.01)
*C10L 10/10* (2006.01)
*C10G 50/00* (2006.01)
*C10L 1/16* (2006.01)
*C10L 1/18* (2006.01)
*C10L 1/185* (2006.01)

(52) U.S. Cl.
CPC .............. *C10L 1/1824* (2013.01); *C10L 10/10* (2013.01); *C10L 1/1641* (2013.01); *C10L 1/1691* (2013.01); *C10L 1/1817* (2013.01); *C10L 1/1852* (2013.01)

(56) References Cited

U.S. PATENT DOCUMENTS

| | | |
|---|---|---|
| 3,981,921 A | 9/1976 | Bohmholdt et al. |
| 4,032,582 A | 6/1977 | Trebillon |
| 4,087,471 A * | 5/1978 | Bowman ................ C07C 29/04 568/899 |
| 4,154,580 A * | 5/1979 | Landis ........................... 44/452 |
| 4,469,905 A | 9/1984 | Inwood et al. |
| 4,684,751 A * | 8/1987 | Trogler ................ C07C 29/04 502/162 |
| 4,886,918 A | 12/1989 | Sorensen et al. |
| 4,956,506 A | 9/1990 | Latimer et al. |
| 5,080,691 A | 1/1992 | Sorensen et al. |
| 5,105,024 A | 4/1992 | McKay et al. |
| 5,231,233 A | 7/1993 | Le et al. |
| 2011/0023355 A1* | 2/2011 | Xu et al. ......................... 44/451 |
| 2012/0016164 A1* | 1/2012 | Kohnz et al. ................. 568/896 |

OTHER PUBLICATIONS

Bernhard Pfeuffer et al., "Heterogeneous reactive extraction for secondary butyl alcohol liquid phase synthesis: Microkinetics and equilibria," CHEMICAL ENGINEERING SCIENCE, 66:4:777-787 (2011).

S. M. Mahajani, et al., "Extractive hydration of n-butene with solid acid catalysts in the liquid phase and under supercritical conditions," CHEMICAL ENGINEERING SCIENCE, 56:5625-5633 (2001).

International Search Report for PCT/IB2012/000145 dated Jun. 29, 2012 (5 pages).

* cited by examiner

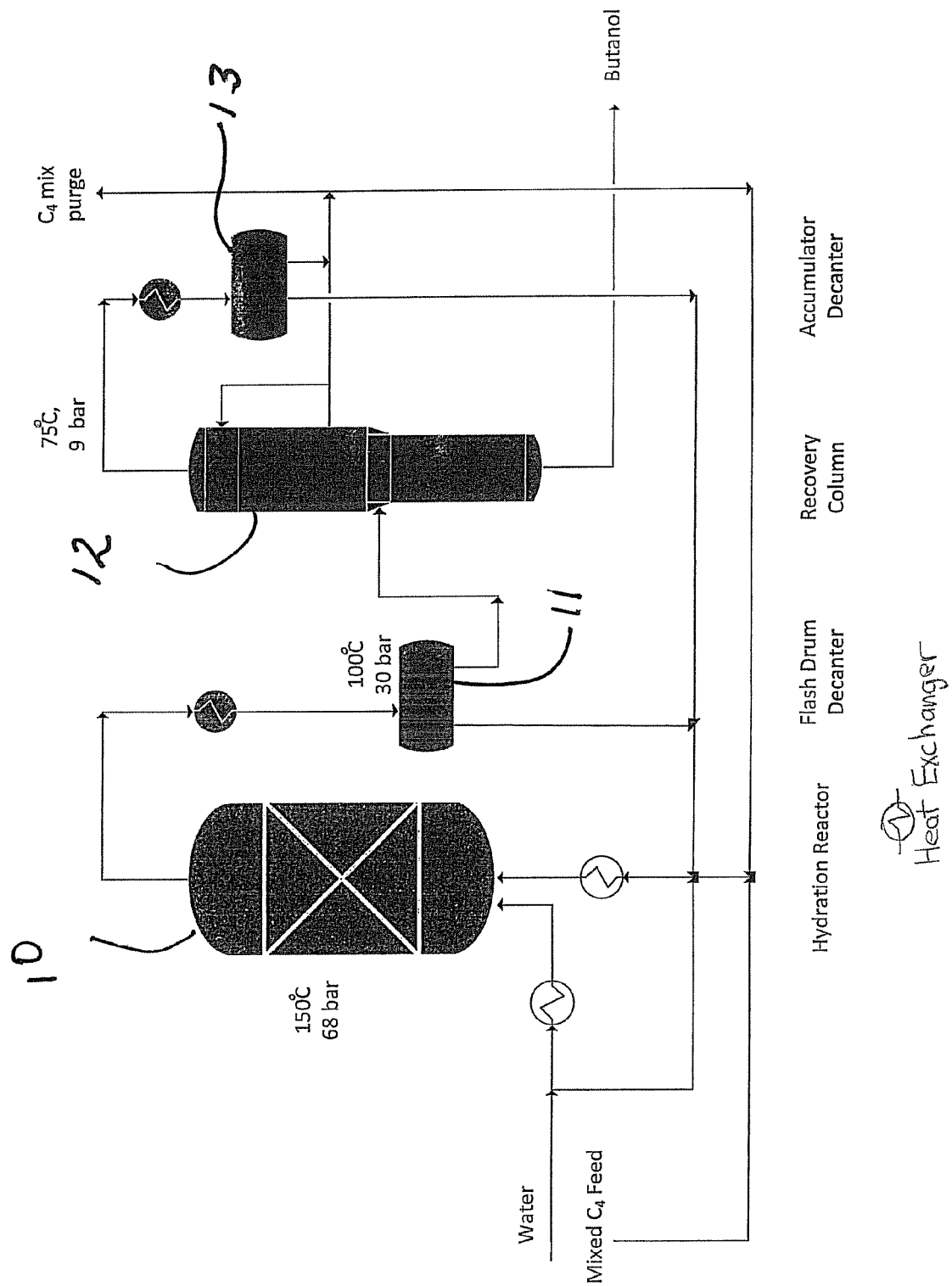

PROCESS FOR THE HYDRATION OF MIXED BUTENES TO PRODUCE MIXED ALCOHOLS

RELATED APPLICATIONS

This application is a §371 of PCT/IB2012/000145 filed Jan. 9, 2012 and claims priority from U.S. Provisional Application No. 61/431,158 filed Jan. 10, 2011, both incorporated by reference in their entirety.

FIELD OF THE INVENTION

This invention relates to a process for the hydration of olefins to produce mixed alcohols, and specifically to the production of a mixture of butanols that are particularly useful as oxygenates for fuels.

BACKGROUND OF THE INVENTION

Substantial quantities of olefins are produced as by-products in hydrocarbon refinery operations, particularly in cracking processes such as fluidized catalytic cracking (FCC) units and steam cracking units. The hydration of olefins to their corresponding alcohols, particularly the C4 olefins, is an industrially important reaction. Various schemes and apparatus have been proposed and adopted for optimizing the reaction conditions in order to increase the yield and/or purity of the alcohols produced.

A typical commercial processes for making 2-butanol from n-butenes operates at relatively high temperatures, i.e., in the range of 145-165° C. in order to obtain acceptable reaction rates. One problem with this type of so-called vapor phase hydration reaction is that it is equilibrium limited. That is, the olefin to alcohol reaction is reversible. This maximum rate of alcohol conversion can be as low as 5% under certain conditions as reported by Denes Kallo and R. Magdolna Mihayi in Applied Catalysis A: General 12 (1995) 45-56. In operation, however, the yields per pass are lower than the theoretical equilibrium amount, so that the yields can be even lower than the low, theoretical maximums.

In order to obtain acceptable yields for the overall process, typical commercial hydration processes recycle the stream containing the olefins. This requires an increase in the total cost of the unit and its operation, due to capital investments associated with, e.g., the compressor(s), as well as the requirement for larger reaction vessels and associated utility costs.

Other commercial processes employ mixed-phase reactions with liquid water so that the alcohol produced is continuously absorbed and the reaction is not equilibrium limited. These processes result in better yields per pass, but require high water/olefin rates and the alcohol/water solution in the reactor tend to dissolve acid catalysts employed in the reaction.

Vapor phase hydration of olefins is described in U.S. Pat. No. 2,130,669, in which olefin(s) and steam are passed through a series of liquid acidic catalyst solutions at high pressure and a temperature that results in the direct distillation of the alcohol formed. The vapors are removed from the reaction vessel and condensed. It is disclosed that a series of bubble plate reactors can be employed to sequentially treat the feed gas that will contain an ever-reduced volume of olefins. Although the examples are limited to ethylene, it is stated that the apparatus and process can be employed to convert higher olefins such as butylenes.

A proposal for improving the overall efficiency of a process for the hydration of olefins that employs a series of at least three, but possibly four or more sequential reactors in a vapor phase reaction scheme is described in U.S. Pat. No. 4,956,506. The olefin feed gas used in the process contain small amounts of ethylene and propylene olefins, i.e., between about 5% and 40% by weight based upon the total feedstream, which also includes methane, hydrogen, and/or various other gases that are inert to the hydration reaction. A suitable feed gas is said to be the tail gas from a fluid catalytic cracker. The FCC tail gas is said to typically contain from about 10 to 20 wt % of ethylene and from 4 to 10 wt % of propylene. A total of four reactors are described, each of which is packed with a perfluorinated ion-exchange polymer having pendant sulfonic and carboxylic groups. After passing through each of the reactors, the converted alcohols, i.e., ethanol and propanol, along with the unreacted feed gases are passed into a vessel containing water, which absorbs the alcohols and passes the remaining olefins and unreacted feed gases to the next reactor.

Although the examples and data reported in U.S. Pat. No. 4,956,560 are limited to the processing of ethylene and propylene, it is claimed, without examples, that butylene and pentylene can also be successfully converted and recovered using the process. However, it is well known that butanols are more soluble in organic solvents than they are in water and thus that their recovery from the process described would not be as effective as for the ethanol and propanol which are highly soluble in water. Ethanol, propanol and t-butanol are miscible with water. The solubility of 2-butanol is 35 g/100 mL at 20° C. For example, isobutanol's concentration in a mix of octyl alcohol and water is significantly different. The partition coefficient is 6.7 as reported in Collander, *Acta Chemicon Scandinavica* 5 (1951) 774-780.

Even though the hydration of olefins has been studied extensively, the main objective of the process of their hydration has been to produce one alcohol rather than mixed alcohols, in order to avoid complication in separation of the different alcohols produced. Prior art methods for olefin hydration are intended to produce pure alcohols. Therefore, either the olefin feed stock used in the hydration reaction must be in an essentially pure form or the hydration process has to be selective to produce only one alcohol product.

U.S. Pat. No. 4,012,456, reports that mixed butenes produce t-butanol via a selective process which hydrates iso-butene to t-butanol. The remaining isomers of butenes are not hydrated and are separated for other applications or LPG.

After removal of isobutene, other butene isomers can be further hydrated into 2-butanol, which can then be converted into methylethylketone (MEK). Mixed quantities of other products can be produced from minor constituents in the feed, such as isopropanol from propane, and side reactions with other olefins.

More recently, bio-butanol has been identified as a desirable second-generation fuel components in place of bio-ethanol. Bio-processes to produce butanols have been reported; however, the butanols are produced by bio-processes that are not particularly efficient, thereby resulting in high costs, and the amounts produced are not likely be sufficient to meet the demands of a growing butanol transportation fuel market.

Petrochemical processes for producing butanol from propylene and carbon monoxide are known, but are very costly. A need exists for an efficient and cost-effective process for producing mixed butanols by hydration.

Also needed is an efficient and cost-effective process for the production of mixed butenes from readily available butene sources in order to meet the current and foreseeable increased future demands for these products on a worldwide basis.

SUMMARY OF THE INVENTION

In accordance with the process of the invention, mixed butenes from a cracking process or raffinates of MTBE or t-butyl alcohol (TBA), are simultaneously hydrated using water, in the presence of a catalyst, to produce mixed butanols, and principally sec-butyl alcohol (SBA) and tert-butyl alcohol (TBA).

The hydration process can be carried out continuously in solution in a suitable reaction vessel and system with mixing of the butenes, water and catalyst, followed by phase separation to recover the butenes with dissolved butanols. The hydration reaction can also be conducted in a fixed bed reactor through which the butenes and water pass to effect the conversion to butanols.

The acid catalyst can be any water soluble or water insoluble organic or inorganic acid, including solid acids as well as liquids. Suitable organic acids include acetic acid, tosylate acid, and perfluorinated acetic acid. Inorganic acids include heteropoly acids, HCl, $H_3PO_4$, and $H_2SO_4$. Solid acids that can be used include ion exchange resins, zeolites and inorganic supported acids.

Other acids that can be used in the process of the invention are the class of heteropoly acids which contain the following constituents:
  a. a metal such as tungsten, molybdenum or vanadium (termed the addenda atom);
  b. oxygen;
  c. an element from the p-block of the Periodic Table, such as silicon, phosphorus or arsenic (termed the hetero atom); and
  d. acidic hydrogen atoms.

It will be understood that the use of water insoluble catalysts, including liquid and solid materials may require a fixed bed process, or a slurry process with agitation at a sufficient intensity to maintain an intimate mixture of the butenes, the water for hydration and the acidic catalyst. A reaction vessel is used that provides a quiescent settling zone adjacent to the fixed bed reactor or the agitation zone for the recovery of the butenes containing the dissolved butanols.

The solubility of the mixed butanols in various catalyzed reaction solutions has been reported by Mehajani, et al., Chem. Eng. Sci., 56 (2001) 5625-5633, the disclosure of which is incorporated herein by reference in its entirety.

The invention has the advantage of using a raw material which is in plentiful supply and for which there is a relatively low demand, i.e., $C_4$ olefin cuts obtained from various refining operations, such as cracking processes. The cuts can contain isomeric mixtures of isobutene, 1-butene and 2-butenes. This enables the upgrading of these $C_4$ olefin cuts in the production of mixed alcohols, and principally secondary and tertiary butanols, thereby reducing the cost and increasing the profitability of their manufacture. Another substantial advantage in using the $C_4$ olefin cuts is the relative ease in transporting and processing them in a liquified state.

Another advantage of the process is that separation of the butene isomers is not required. In the practice of the process of the invention, the entire fraction of butenes can be utilized for manufacture of useful gasoline additives, e.g., oxygenates and octane enhancers. The lower Reid Vapor Pressure (RVP) of the butanols will also permit larger quantities of pentane to be present in the gasoline blend and still meet federal and state regulatory requirements.

The entire butene fraction containing 1-butene, 2-trans-butene, 2-cis-butene and isobutene is hydrated in the presence of an acidic catalyst to form mixed butanols. The unconverted butenes are recycled back to the hydration process.

Although butenes are sparingly soluble in water, they form separate phases under the reaction conditions of the process of the invention, especially when the mixed butenes are used in a sufficiently large quantity and in the concentration phase. Since the butanols produced are relatively non-polar and have a favorable distribution in the concentrated butenese phase, as the reaction proceeds and significant amounts of butanols are formed, the butanols undergo solvent extraction and are dissolved in the butene-rich organic phase. This simultaneous extraction during the course of the reaction serves to continuously shift the reversible reaction in the direction of continued alcohol formation.

The mixed butanols produced by the process of the invention have good petroleum blending octane characteristics and they can also be used in combination as petroleum additives. The present invention thus provides a highly cost-effective process by utilizing mixed butenes without separation to produce a product stream of mixed butanols.

Furthermore, the invention provides a hydration process to produce highly desirable butanol octane enhancers, as well as oxygenates useful as gasoline components from relatively inexpensive butene feedstocks.

Mixed butanols can be used as combustible neat fuels, as well as octane enhancers and/or to oxygenate fuel and constituents in gasoline, diesel, jet fuel, aviation gasoline, heating oil and bunker oil. The mixed butanols consist of n-butanol, 2-(+/−)-butanol, isobutanol and tert-butanol, preferably 2-(+/−)-butanol and tert-butanol. The primary benefits of using mixed butanols as oxygenate fuel constituents or neat fuel include but are not limited to, increased combustion efficiencies and reduced emissions of harmful gases and airborne soot.

Other benefits of the mixed butanol fuels that (a) their BTU energy content is closer to the energy content of gasoline than that of methanol/ethanol based fuels; (b) butanols can be used as octane enhancers to replace tetraethyl-lead, MTBE, methanol, ethanol, MMT and other octane boosters without the negative environmental effects associated with those additives; (c) butanols have low and stable Reid Vapor Pressure blending characteristics; (d) butanols are much less corrosive than methanol/ethanol and existing storage and transportation facilities can be used; (e) butanol based fuels can be used in existing engines without modification; and (f) butanols are understood to be relatively low toxicity components and are normally readily biodegradable.

BRIEF DESCRIPTION OF THE FIGURES

FIG. 1 depicts an apparatus which can be used in the practice of the invention.

DETAILED DESCRIPTION OF THE INVENTION

The process of the invention will be further described with reference to the attached schematic drawing. The temperature of the water and mixed butene ($C_4$) feed streams are controlled by heat exchangers prior to their introduction into the hydration reaction "10" that also contains the acid catalyst and water at predetermined concentrations. Exemplary reaction conditions are about 150° C. and 68 bar. As shown, water is also added to the mixed butenes before their introduction into the hydration reactor.

The reaction products are withdrawn from the reactor and passed through a heat exchanger to adjust the temperature of the product stream prior to introducing it into the flash drum decanter "11", which is maintained at exemplary operating conditions of 100° C. and a pressure of about 30 bar. The hydrated reaction product stream is then introduced into a recovery column 12 for release of lighter constituents from the top of the column and recovery of the butanol products as the bottoms. The column is preferably operated at, e.g., about 75° C. and a pressure of about 9 bar.

The lighter constituents are subjected to heat exchange before being introduced into the accumulator decanter 13. The output of the accumulator decanter is divided into a purge mixture and a recycle stream that is returned to the hydration reactor.

It will be understood that the arrangement of the apparatus and the indicated operating conditions are those presently preferred, and that other processes and systems can be employed to achieve comparable results. It will also be understood that the presence of other constituents in the feedstream, such as C3 and C5 olefins, can be tolerated, but that minor modifications in operating conditions and arrangements of the apparatus may be required. Such modifications and variations will become apparent to those of ordinary skill in the art from the present description.

EXAMPLES

The following examples are given for the purpose of illustrating the process of this invention. However, it is to be understood that these examples are merely illustrative in nature, and that the present process is not limited thereto.

All of the butanols utilized in the following examples were purchased directly from commercial suppliers of fine chemicals and used without any purification as GC standards. All of the pure butenes were also purchased from commercial suppliers and used without purification. All of the acids, ionic exchange resins, phase transfer agents and ionic liquids were similarly purchased. Zeolites were synthesized according to published methods. The mixed butenes were obtained from a refinery and contained no additives. The composition of the mixed butenes was determined by GC-MS as detailed below and the concentrations were determined by the method described prior to Table 1.

Butene Identification and Quantification

Butene identification and quantification was carried out using a commercially available gas chromatograph equipped with a flame ionization detector (FID) and a split/splitless injector. A 250 μL gas sample was injected in the splitless mode. Semi-quantitative results were obtained by normalization of the peak area to the full chromatogram. All samples are analyzed in triplicate and an average value was reported.

Butanol Quantification

Hydration products were quantified using a method that is described below and the same gas chromatograph described previously, equipped with an autosampler.

Butene Hydration Examples

Deionized water (200 g), acid (4 g) as shown in Table 2, and optionally, a phase transfer agent, i.e., Pr4NBr (4 g) were all placed in a Parr autoclave. The autoclave was sealed and purged five times with nitrogen at 50 psi. Next, 10 mL of pure 2-trans-butene or 15 mL of mixed butenes from a local refinery were charged to the autoclave under 50 psi of nitrogen gas. The molar ratio of water-to-butenes and the mole ratio of butenes-to-acid are set forth in Tables 2 and 3. The autoclave was heated and maintained at a predetermined temperature for a period of 2-3 hours. At the end of this time, heating was discontinued and the autoclave was allowed to return to room temperature over a period of 2-3 hours before the excess pressure was vented. The autoclave was then opened and the reaction mixture was recovered. The conversion rates were determined by means of gas chromatography. The conversion rates for different hydration conditions are also provided in Tables 2 and 3, with a 100% selectivity to butanols unless other cited.

The 2-trans-butene used in the tests that provided the data reported in Table 2 was purchased from a local commercial source and subjected to the indicated hydration conditions without purification.

TABLE 2

Hydration conditions and conversion yield of 2-trans-butene*

| Exp. No. | Catalyst | Temp (° C.) | Psure (psi) | Time (Hr) | H2O/ C4 | C4/ Acid | Conv % |
|---|---|---|---|---|---|---|---|
| 1 | ZSM5 activated at 350 C. under vacuum | 150 | 170 | 2 | 2.6 | | 0.21 |
| 2 | ZSm5 activated at 500 C. | 150 | 240 | 2 | 2.1 | | 0.35 |
| 3 | WO3/Silica | 200 | 360 | 2 | 21 | 104 | 0.2 |
| 4 | H3PO4 | 150 | 480 | 3 | 10 | 34 | 0.5 |
| 5 | H2SO4 | 150 | 178 | 2 | 78 | 5 | 4.3 |
| 6 | Amberlite 15/ H3PO4 (2 g) | 150 | 160 | 2 | 104 | | 6 |
| 7 | Amberlite 15 | 150 | 160 | 2 | 104 | | 5.4 |
| 8 | MoO3 on silica | 200 | 160 | 2 | 104 | 16 | 4.1 |
| 9 | WO3/Silica | 120 | 150 | 5.5 | 104 | 38 | 0.1 |
| 10 | WO3/Silica | 200 | 220 | 3 | 104 | 41 | 0.64 |
| 11 | H3PO4 | 150 | 160 | 3 | 104 | 6 | 0.52 |
| 12 | AcOH (2.6 g) | 150 | 250 | 3 | 52 | 1.6 | 0.23 |
| 13 | AcOH (4 g)/Pr4NBr (4 g) | 150 | 160 | 6 | 104 | 1.6 | 28.6 |
| 14 | AcOH (2)/Pr4NBr (20 g) | 150 | 180 | 3 | 104 | 3.2 | 17.5 |

The mixed butene feeds used in the tests reported in Table 3 were obtained from a local refinery and subjected to the indicated hydration conditions without purification.

TABLE 1

| Contents of the mixed butenes (wt %) | | | | | | | | | | |
|---|---|---|---|---|---|---|---|---|---|---|
| C3 = | C3 | C4 = (total) | 2-t-C4 = | 1-C4 = | 2-c-C4 = | i-C4 = | i-C4 | n-C4 | i-C5 | n-C5 |
| 16.32 | 4.22 | 48.58 | 24.39 | 4.61 | 14.64 | 4.94 | 22.00 | 7.48 | 1.21 | 0.19 |

TABLE 3

Hydration conditions and conversion rates of the mixed butene feeds.

| Exp. No. | Reactants Catalyst | Reaction Conditions | | | | | | Based on ASD Data | | |
|---|---|---|---|---|---|---|---|---|---|---|
| | | temp (C) | P (psi) | time (H) | H2O/C4 | C4/Acid | Conv % | 2-OH/t-OH | 2-OH Conv % | t-OH Conv % |
| 1 | ZSM5 activated at 500 C 24 h and grinded | 150 | 200 | 3 | 138 | | 14.2 | 3.1 | 12 | 34 |
| 2 | ZSM5 activated at 500 C 24 h and grinded | 150 | 200 | 5 | 138 | | 6 | 0.2 | 1.3 | 48 |
| 3 | Dowex 50WX8 hydrogen form | 150 | 200 | 3 | 145 | | 10.2 | 2.4 | 8 | 30 |
| 4 | Dowex 50WX8 hydrogen form | 150 | 540 | 24 | 23 | | 11.1 | 4.1 | 10 | 21 |
| 5 | Dowex 50WX8 hydrogen form | 150 | 200 | 5 | 138 | | 13.4 | 2 | 10 | 44 |
| 6 | Dowex 50WX8 hydrogen form | 120 | 200 | 5 | 138 | | 11.9 | 1.8 | 8.5 | 42 |
| 7 | Dowex 50WX8 hydrogen form re-use | 120 | 200 | 5 | 138 | | 16.6 | 2.8 | 13.6 | 43 |
| 8 | Amberlite CG-120-II | 120 | 160 | 3 | 138 | | 6.8 | 0.8 | 3.4 | 36 |
| 9 | Amberlite CG-120-II | 100 | 160 | 8 | 138 | | 6.3 | 0.5 | 2.5 | 41 |
| 10 | Amberlite 15 50 g | 150 | 570 | 3 | 4 | | 1.9 | 1.7 | 1.3 | 7 |
| 11 | Amberlite 15 | 150 | 200 | 3 | 138 | | 9.9 | 2.5 | 7.9 | 28 |
| 12 | trifluoroacetic acid | 150 | 200 | 5 | 138 | 9 | 13.7 | 2.1 | 10.3 | 43 |
| 13 | H3[P(W3O10)4]×H2O | 150 | 200 | 3 | 138 | 115 | 9.8 | 1.1 | 5.7 | 46 |
| 14 | H3[P(W3O10)4]×H2O | 150 | 200 | 5 | 138 | 115 | 8.7 | 1.2 | 5.2 | 39 |
| 15 | H3[P(W3O10)4]×H2O | 150 | 570 | 3 | 4 | 74 | 9.6 | 2.3 | 7.5 | 28 |
| 16 | Tungstosilicic acid hydrate | 150 | 200 | 3 | 138 | 55 | 6.4 | 1 | 3.5 | 32 |
| 17 | carbon black 10 g/H3PO4 2 g | 150 | 200 | 4 | 138 | 115 | 2.9 | 1.8 | 2.1 | 10 |
| 18 | carbon black 10 g/H3PO4 6 g | 150 | 200 | 4 | 138 | 115 | 6.4 | 0.9 | 3.3 | 34 |
| 19 | clay 10 g/H3PO4 6 g | 150 | 200 | 5 | 138 | 115 | 5.6 | 0.5 | 2.1 | 37 |

A gasoline with 45% light straight run naphtha (LSRN) and 55% reformate was used as a standard to test the behaviors of butanols at the same additive volume (15%). The ASTM tests methods used for the fuel tests are identified in Table 4, where MON is motor octane number and RON is research octane number.

TABLE 4

Test methods

| Test method | physical property |
|---|---|
| ASTM D-2699 | RON |
| ASTM D-2700 | MON |
| ATSM D-323 (gasoline) ATSM D-5191 (diesel) | RVP |
| ASTM D 4052 ASTM D 5291 | Specific Gravity |
| ASTM D 4840(diesel) ASTM D 4809 (gasoline) | BTU (Heat of Combustion) |

The ratios of components and the test results are set forth in Table 5.

The examples demonstrate that butanol can be blended into gasoline as a substitute for MTBE. The "petro-butanol" (2-butanol/t-butanol) blended gasoline had a BTU value that was similar to MTBE blended gasoline. Although the RVP and RON values are slightly lower, they are sufficient to allow the use of the product as oxygenate and octane enhancers to replace MTBE.

TABLE 5

Butanol effects on gasoline

| | Gasoline Tests | RVP (psi) | BTU (MJ/L) | MON | RON |
|---|---|---|---|---|---|
| 1 | 45% LSRN/55% reformate | 7.05 | 16970 | 81.4 | 87.7 |
| 2 | MTBE 15% | 7.41 | 16280 | 85.1 | 92.7 |
| 3 | 2-butanol/t-butanol (1:1) 15% | 6.98 | 17514 | 83.2 | 91 |

Although various embodiments of the invention have been described above and in the attached drawing, other modifications and variations will be apparent to those of ordinary skill in the art from this description, and the scope of the invention is to be determined by the claims that follow.

The invention claimed is:

1. A process for the production of mixed alcohols from a liquid feedstream of mixed butenes, said mixed butenes consisting of 1-butene, 2-cis butene, 2-transbutene and isobutene, wherein a majority of the butene in said feedstream of mixed butenes is 2-trans-butene, comprising:
   a. providing a fixed bed reactor containing an acid hydration catalyst and a phase transfer agent;
   b. introducing the liquid mixed butene feedstream and water into the fixed bed reactor and into contact with the hydration catalyst under conditions favorable to hydration of the mixed butenes, to form mixed butanols, said mixed butanols comprising a majority of 2-butanol and t-butanol;
   c. recovering unreacted mixed butenes enriched with mixed butanols from the fixed bed reactor;
   d. separating the mixed butanols from the mixed butenes to forma mixed butanol product stream and a lean mixed butene stream;
   e. recovering the mixed butanol product stream; and
   f. returning the lean mixed butene stream to the fixed bed reactor.

2. The process of claim 1, where the fixed bed catalyst is in a downflow, upflow or counter-current flow reactor.

3. The method of claim 1, wherein said acid hydration catalyst is a water soluble acid.

4. The method of claim 3, wherein said organic acid catalyst is selected from the group consisting of acetic acid, tosylate acid, and perflourinated acetic acid.

5. The method of claim 3, wherein the water soluble acid is selected from the group consisting of HCl, $H_3PO_4$, $H_2SO_4$ and a heterotopoly acid.

6. The method of claim 1, wherein said acidic catalyst is a solid acid selected from the group consisting of an ionic exchange resin, an acidic zeolite, and a metal oxide.

7. The process of claim 1, wherein said phase transfer agent is $Pr_4NBr$.

* * * * *